United States Patent [19]

Jones et al.

[11] 4,088,907

[45] May 9, 1978

[54] PIEZOELECTRIC ACOUSTIC EMISSION INSTRUMENTATION

[75] Inventors: Charles H. Jones, Pasadena; George R. Douglas, Arnold, both of Md.

[73] Assignee: Westinghouse Electric Corp., Pittsburgh, Pa.

[21] Appl. No.: 736,799

[22] Filed: Oct. 29, 1976

[51] Int. Cl.² .......................................... H01L 41/04
[52] U.S. Cl. .................................. 310/333; 310/319; 310/366; 73/522; 73/88.5 SD
[58] Field of Search .................. 310/8.2, 8.3, 9.5, 9.6, 310/9.8, 8.1, 8.4; 73/52, 67, 552, 555–558, 67.3, 70, 71.5 US, 88.5 R, 88.5 SD, DIG. 4

[56] References Cited

U.S. PATENT DOCUMENTS

| | | |
|---|---|---|
| 2,927,300 | 3/1960 | Smith ............................. 310/8.4 UX |
| 3,437,851 | 4/1969 | Cady ................................ 310/9.8 X |
| 3,566,163 | 2/1971 | Fisher et al. ........................ 310/8.3 |
| 3,739,202 | 6/1973 | Cady ................................... 310/8.3 |
| 3,805,097 | 4/1974 | Yanchich et al. ................ 310/9.5 X |

*Primary Examiner*—Mark O. Budd
*Attorney, Agent, or Firm*—D. Schron

[57] ABSTRACT

A detector of acoustic emissions from a structure includes a piezoelectric element responsive to both compressional wave energy and to shear wave energy from any direction so that the source of the acoustic emission may be determined.

16 Claims, 21 Drawing Figures

NOTE: L=LONGITUDINAL WAVE  S=SHEAR WAVE

| TIME MONTH, DAY, HR. MIN. | TRANSDUCER NUMBER | AVERAGE POWER FROM EACH TRANSDUCER | | |
|---|---|---|---|---|
| | | 2.5 MINUTES | HOUR | DAY |
| 7 - 24 - 14 : 35 | 1 | 10 | 15 | 9 |
| | 2 | 8 | 8 | 7 |
| | 3 | 5 | 10 | 5 |
| | 4 | 210 | 120 | 60 |
| | 5 | 22 | 25 | 20 |
| | 6 | 4 | 6 | 6 |
| | 7 | 7 | 7 | 7 |
| | ⋮ | ⋮ | ⋮ | ⋮ |
| | 32 | 13 | 16 | 14 |
| | 33 | 20 | 15 | 15 |
| 7 - 24 - 14 : 40 | 1 | 10 | 15 | 9 |
| | 2 | 110 | 8 | 7 |
| | 3 | 6 | 10 | 5 |
| | 4 | 218 | 124 | 65 |
| | 5 | 20 | 25 | 20 |
| | 6 | 8 | 7 | 6 |
| | 7 | 5 | 7 | 6 |
| | ⋮ | ⋮ | ⋮ | ⋮ |
| | 32 | 14 | 16 | 14 |
| | 33 | 18 | 15 | 14 |
| 7 - 24 - 14 : 45 | 1 | 11 | 14 | 9 |
| | 2 | 8 | 9 | 7 |
| | 3 | 7 | 10 | 5 |
| | 4 | 228 | 129 | 70 |

PIEZOELECTRIC ACOUSTIC EMISSION INSTRUMENTATION

BACKGROUND OF THE INVENTION

1. Field of the Invention

The invention in general relates to apparatus for detecting incipient flaws in structures.

2. Description of the Prior Art

Acoustic emission signals are sometimes generated in structures due to stressing of the structural material as well as by crack initiation and/or growth. These acoustic emissions are high frequency elastic waves that travel through the material and are indicative of possible structural degradation.

Accordingly, acoustic emission instrumentation systems are provided for monitoring the structural integrity by the use of an array of acoustic emission detectors placed over a structure in conjunction with a triangulation system which uses information on the detector position coordinates, the stress wave arrival time at the detectors, and various parameters to compute the location of an acoustic emission source. Once located, the suspect zone of activity is pinpointed for later diagnostic inspection which may be done using high resolution ultrasonic imaging techniques or X-rays.

One type of transducer assembly which may be utilized as a passive listening device to detect acoustic emission is described in U.S. Pat. No. 3,935,484. The assembly utilizes a piezoelectric element which is coupled to an acoustic window of the assembly and is compressed against it. The transducer element is responsive to surface displacement in a normal direction caused by an acoustic emission.

Under certain circumstances, it would be desirable to provide a detector which not only was responsive to compressional wave energy but also shear wave energy so as to provide somewhat more information relative to the acoustic emission. One way of accomplishing this is to place additional shear wave detectors in the general area of the compressional wave detector. However, this arrangement adds to the complexity and total cost of the system. One type of measuring cell described in U.S. Pat. No. 3,566,163 is sensitive to both shear and compressional forces, and is packaged in a self-contained integral assembly. It is, however, used for force or acceleration measurements. The measuring cell utilizes six piezoelectric discs with interposed electrodes, and such arrangement if it were adapted to detect acoustic emissions would exhibit a relatively low efficiency due to the many couplings through the interfaces and electrodes, and consequent distortion of meaningful output signals.

SUMMARY OF THE INVENTION

In the present invention, a transducer housing which may be coupled to a structure under observation includes an acoustic window and a piezoelectric transducer element positioned behind the window so as to be responsive to acoustic energy transmitted by an acoustic emission in the structure. The transducer element is oriented with its poled direction perpendicular to the acoustic window and includes three pairs of electrodes, a first pair being disposed on the top and bottom surfaces so as to be responsive to compressional wave energy transmitted through the window. A second pair of electrodes is disposed opposite one another on the side surface of the transducer so as to be responsive to shear wave energy, and a third pair of electrodes disposed opposite one another on the side surface is angularly displaced from the second pair of electrodes to be also responsive to shear wave energy transmitted through the window.

The signals thus provided by the plurality of pairs of transducers are then utilized in conjunction with the signals from other detectors for computing the location of acoustic emissions.

This computation may be made by first squaring the three voltage signals provided by the electrode pairs and then adding the squared signals to obtain a signal proportional to the received power in the acoustic waves.

DESCRIPTION OF THE PREFERRED EMBODIMENT

Figure 1A:
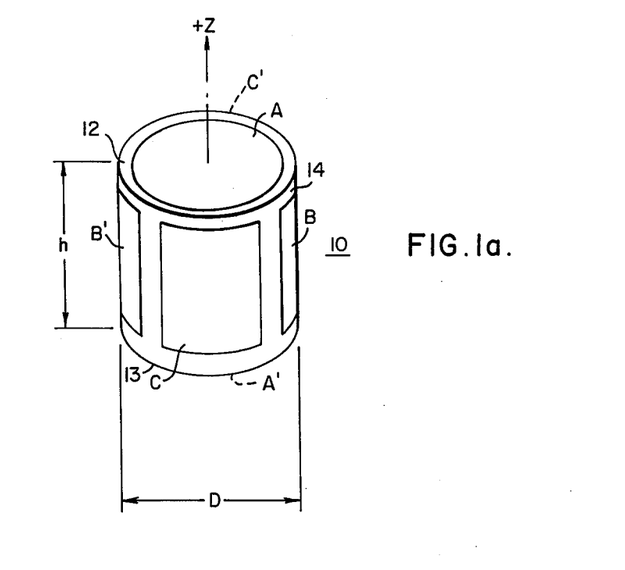
FIGS. 1a and 1b illustrate two shapes of piezoelectric elements which may be utilized herein.

FIG. 1a illustrates a piezoelectric element 10 which includes top, bottom, and side surfaces 12, 13, and 14, and is of a generally circular cylindrical shape. Element 10 may be a PZT (lead zirconate titanate) material having a longitudinal axis Z and being poled in the same direction as the axis. Other piezoelectric materials such as lead metaniobate may be used in place of PZT but the material should be isotropic or at least have the same response characteristics in the two orthogonal directions perpendicular to the direction of poling.

A first pair of electrodes A and A' are positioned opposite one another on the top and bottom surfaces, and for the poling direction will provide an output signal in response to compressional wave energy. A second pair of electrodes B and B' are positioned opposite one another on side surface 14 and will provide a maximum output signal in response to shear wave energy in a first direction. Angularly displaced from the second pair of electrodes, and preferably by 90°, is a third pair of electrodes C and C' diametrically opposed on the side surface 14 and is responsive to shear wave energy such that a maximum output signal will be provided when the shear wave energy is in a second direction perpendicular to the first direction.

A typical piezoelectric element for detection of acoustic transmission would have a height $h$ approximately equal to a half wavelength in the element at the primary frequency of interest and a diameter D approximately equal to a half wavelength or an odd multiple of half wavelengths of the shear wave in the structural material under observation.

Figure 1B:
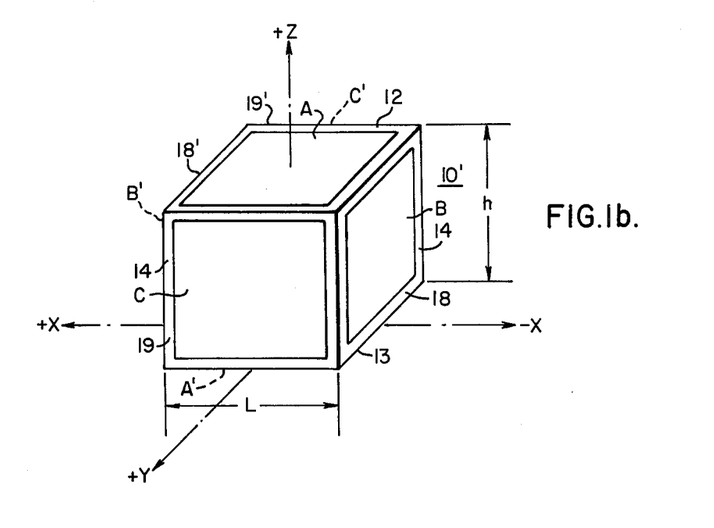

FIG. 1b illustrates another form of piezoelectric element 10' similarly including top, bottom, and side surfaces 12, 13, and 14, with however the side surface 14 being formed from opposed faces 18 and 18' and 19 and 19'. The element is poled in the direction of the longitudinal axis Z and the three pairs of electrodes are positioned such that electrodes A and A' provide an output signal in response to compressional wave energy and the other two pairs of electrodes B and B' and C and C' produce output signals in response to shear wave energy. The dimensions are the same as the element described in FIG. 1a with the dimension L being equivalent to the dimension D.

Figure 2:
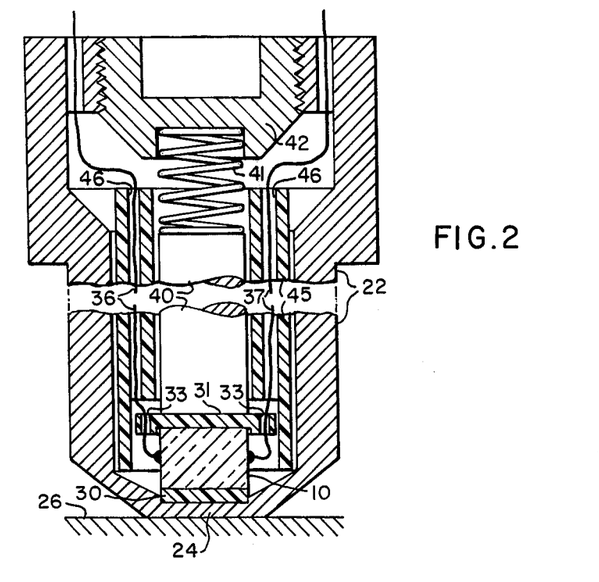
FIG. 2 is a cross-sectional view of a transducer housing in which the piezoelectric element is mounted.

FIG. 2 illustrates the piezoelectric element 10 positioned within a case or holder 22 having an acoustic window 24 at one end thereof for transmission of acoustic energy emanating from an acoustic emission within structure 26.

The piezoelectric element 10 is held firmly in position between two electrically insulating discs 30 and 31 and in order to achieve good shear wave coupling, insulating disc 30 may be bonded to both the window 24 and element 10.

Insulating disc 31 has a plurality of apertures 33 therein for passage of electrode leads, two of which 36 and 37 are illustrated. Leads from the remaining two pairs of electrodes would be brought out through four other apertures arranged around the disc 31.

In order to absorb undesired acoustic reflections, and to act as a reaction mass, there is provided a damping block member 40 urged into compressional engagement with the lower assembly by means of spring 41 and cap 42.

An insulating cylinder 45 surrounds the piezoelectric element 10, disc 31, backing member 40 and includes a number of apertures 46 for passage of the leads connected to the transducer electrodes.

In general, the case 22 is typically formed of a metallic member and from an electrical standpoint is nominally at ground potential. In actual operation, however, the potential of the case may vary somewhat and in order to eliminate any noise pickup due to this variation in the potential of the case, it is preferable that insulating discs 30 and 31 be of equal thickness so that the capacity to ground from electrodes A and A' will be equal.

Figure 3:
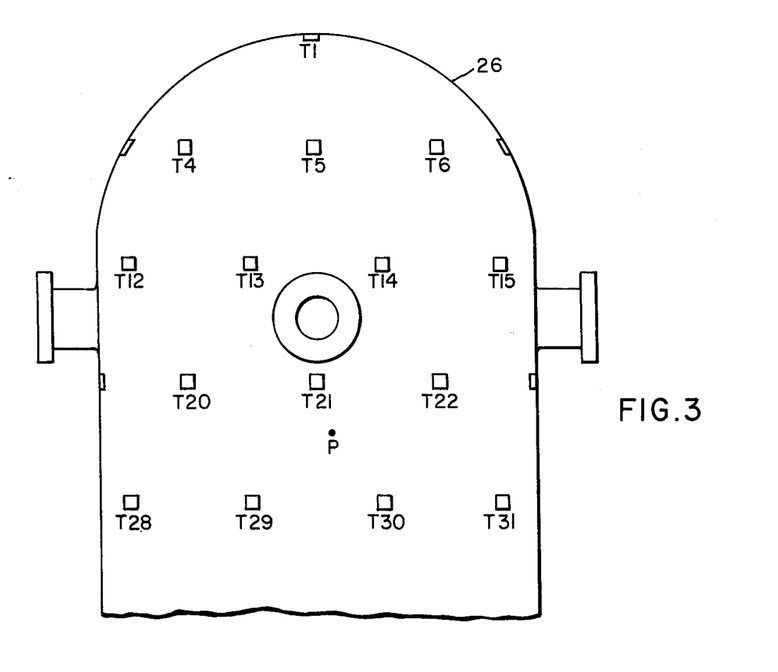
FIG. 3 illustrates a structural member with an array of detectors on its surface.

The apparatus of FIG. 2 forms a detector of acoustic emissions and in actual use, a plurality of such detectors will be positioned on a structure under observation, such as illustrated in FIG. 3. Structure 26 may be for example, a nuclear reactor pressure vessel which includes on the surface thereof an array of detectors T each one being of a construction as illustrated in FIG. 2.

Figure 4:
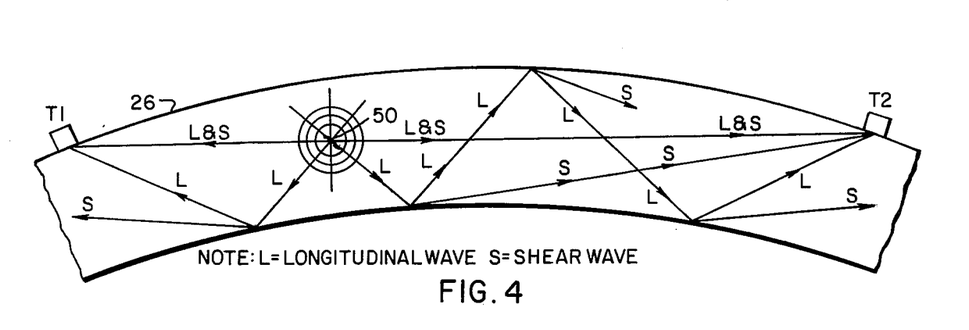
FIG. 4 is a cross-sectional view through a wall of a structural member illustrating an acoustic emission therein.
Figure 5:
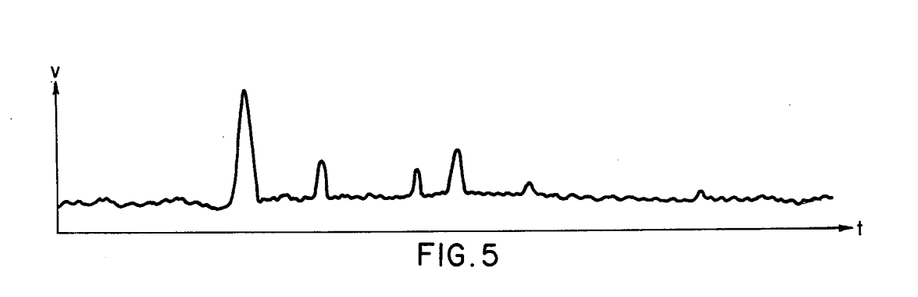
FIG. 5 illustrates a typical waveform provided by the transducer arrangement herein.

A wall portion of structure 26 is illustrated in cross-section in FIG. 4, together with two detector units T1 and T2 on the surface thereof. A region of high local stress in the region depicted at 50 causes acoustic emission of such nature that longitudinal (L) and/or shear waves (S) are radiated. A region of high local stress may produce shear emission or longitudinal emission, and often both types of emission may be simultaneously emitted. What is received at the various detectors however, is a complex waveform, such as illustrated in FIG. 5, due to the fact that shear waves do not propagate at the same velocity as longitudinal waves, and due to the fact that the detectors pick up not only direct waves, but reflected waves, and multiple reflected waves, at different points in time. In general at each reflection of a shear wave a compressional wave is generated and at each reflection of a compressional wave a shear wave is generated. The structure illustrated in FIG. 2 will detect not only the compressional waves but also shear waves from different and varying directions.

Figure 6A:
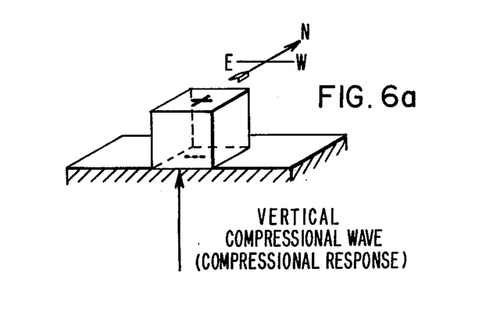
FIGS. 6a to 6i illustrate the response of the transducer to the three components of a compressional wave and the six components of a shear wave.

The response of transducer element to both longitudinal and shear signals will be explained with reference to FIGS. 6a-i. A transducer of the type shown in FIG. 1b poled in a vertical direction, is assumed to be located on top of a horizontal slab of metal and is oriented so that the four sides face North, East, South and West. A longitudinal compressional wave arriving from any direction can be considered to be made up of three orthogonal vector components: a vertical vector, a horizontal E-W vector, and a horizontal N-S vector. FIGS. 6a, b and c illustrate the signals resulting from these three components. The vertical component produces a compressional response and an ac output between the top and bottom electrodes. The + and − symbols indicate the location of the electrodes which yield an output signal. The E-W component of the longitudinal wave produces a small shear force on the transducer due to its inertia and an output voltage between the E-W electrodes. Similarly the N-S longitudinal wave produces a small shear response and an output between the N-S electrodes.

Now consider a shear wave arriving at the transducer from any direction and with any shear orientation. Such a signal can be considered to be made up of three orthogonal signals: vertical, horizontal E-W and horizontal N-S. The vertical signal can be broken into two component signals, one with a N-S shear direction and one with an E-W shear direction. These are illustrated in FIGS. 6d and g. The output signal voltage gradient is orthogonal to both the poling direction and the shear vector. Consequently, in FIG. 6d, the vertical shear wave with a N-S shear vector produces an ac output from the E-W electrodes. Similarly, in FIG. 6g, the vertical shear wave with an E-W shear direction produces an output from the N-S electrodes.

Figure 6B:
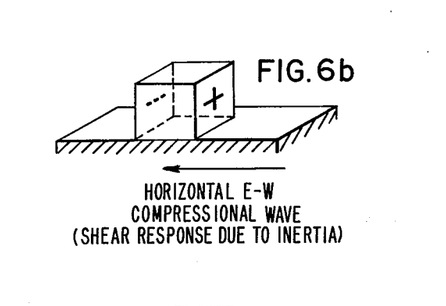
Figure 6C:
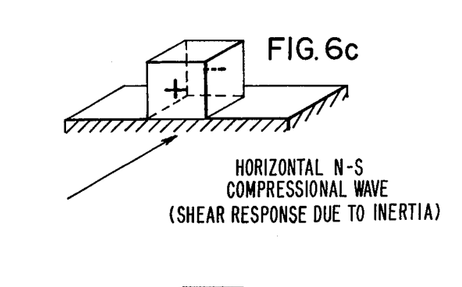
Figure 6D:
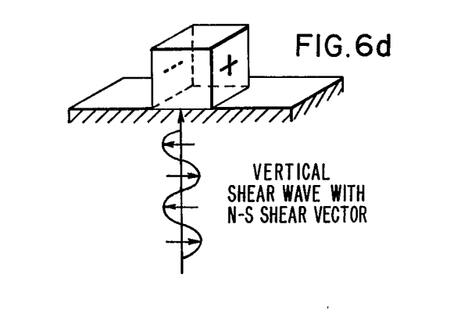
Figure 6E:
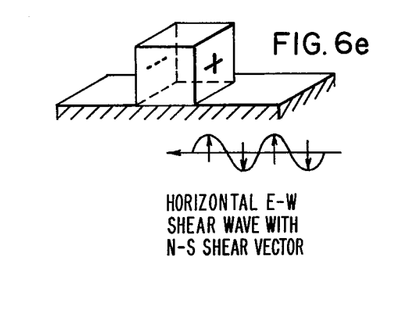
Figure 6F:
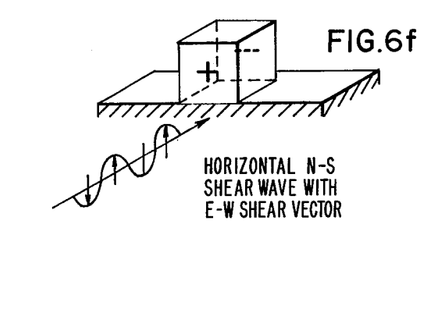
Figure 6G:
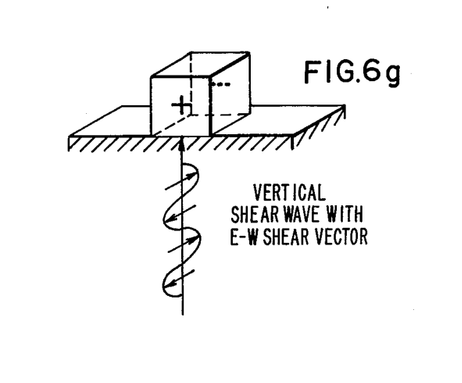
Figure 6H:
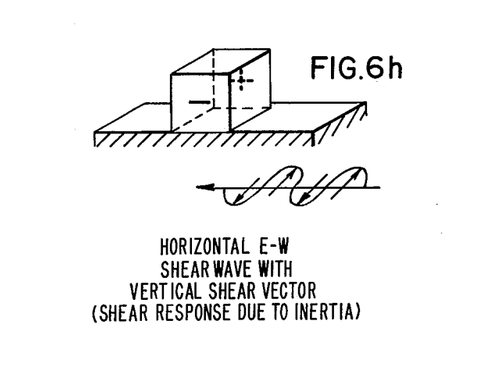
Figure 6I:
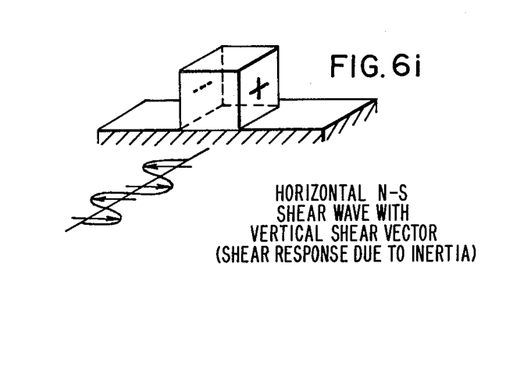

In a similar manner, the E-W shear signal can be considered to be made up of a component having a N-S shear direction and a component with a vertical shear direction as illustrated in FIGS. 6e and h. The E-W shear wave with the N-S shear vector produces an output from the E-W electrodes. The E-W shear wave with the vertical shear vector produces a shear response due to the transducer inertia and consequently an output between the N-S electrodes. The N-S shear signal can also be considered to be composed of one signal with horizontal E-W shear vector, FIG. 6f, and one signal with vertical shear vector, FIG. 6i. In FIG. 6f the outputs are between the N-S terminals and in FIG. 6i the outputs are between the E-W terminals.

In general, the outputs illustrated in FIGS. 6b, c, h and i will be small compared to the wave components shown in FIGS. 6a, d, e, f and g since they depend on the inertia of the transducer element and that of the backing mass.

A preferred thickness for the transducer element is one-half wavelength for the longitudinal mode at the frequency of primary interest. For example, at a frequency $f = 500$ KHz using a ceramic such as PZT with a longitudinal (compressional) velocity $v_{cc} = 2.2 = 10^5$ inches/second, the wavelength is $$\lambda_{cc} = (v_{cc}/f) = (2.2 \times 10^5/5 \times 10^5) = 0.44 \text{ inches.}$$

A preferred transducer thickness is then $$h = \lambda_{cc}/2 = 0.22 \text{ inches}$$

A preferred width and length for the element is one-half wavelength for the shear mode in the vessel material. For example, when detecting acoustic emission at 500 KHz in a mild steel vessel having a shear velocity $v_{ss} = 1.3 \times 10^5$ in/sec the wavelength is $$\lambda_{ss} = (v_{ss}/f) = (1.3 \times 10^5/5.0 \times 10^5) = 0.26 \text{ inch.}$$

A preferred length or width dimension is then $$L = \lambda_{ss}/2 = 0.13 \text{ inch.}$$

From the preceding, it is evident that a longitudinal or shear wave from any direction will produce an output from the proposed transducer. The received power from each pair of terminals is proportional to the square of the output voltage after the signal is amplified and detected. Consequently, it is desirable to square each of the voltages before combining the three signals.

Figure 7:
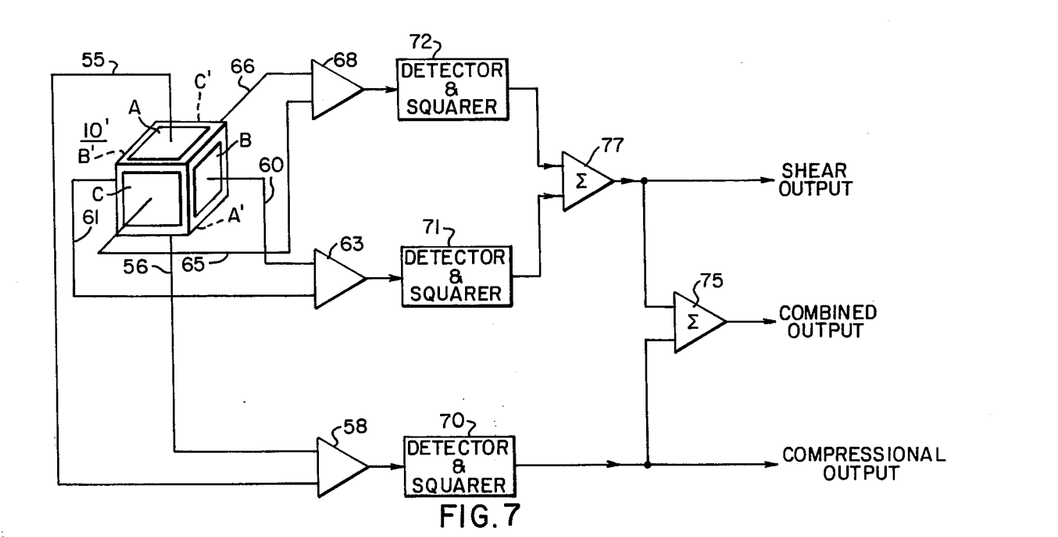
FIG. 7 is a block diagram illustrating the processing of the signals provided by th piezoelectric element.

FIG. 7 illustrates in block diagram form the initial processing of the compressional and shear wave signals. Leads 55 and 56 are connected to respective compressional wave electrodes A and A' and conduct a first signal provided thereby to a balanced amplifier 58. A first shear wave signal is conducted by leads 60 and 61 from respective electrodes B and B' to balanced amplifier 63. The other shear wave signal from electrodes C and C' is conducted by leads 65 and 66 to balanced amplifier 68. After amplification, the three signals are detected and squared in units 70 to 72. The outputs of units 71 and 72 are added together in summer 77 and that output is added to the output of unit 70 in summer 75.

The output from summer 77 may be considered as primarily a shear output and the output from squarer 70 as primarily a compressional output. By combining these two signals in summer 75 a signal is obtained that is proportional to the total power received by the transducer.

Figure 8:
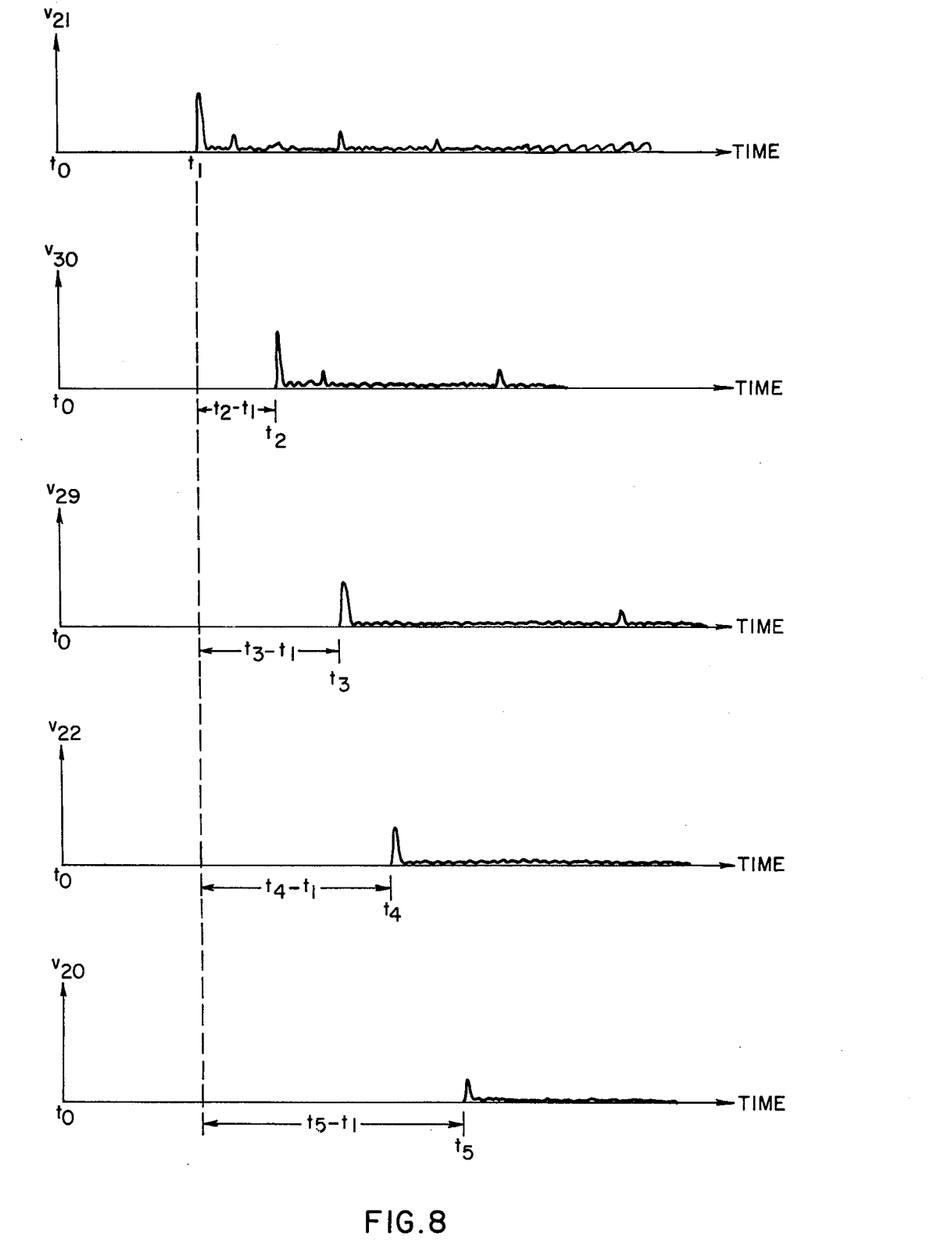
FIG. 8 illustrates five signals that might be received by five of the transducers illustrated in FIG. 3 due to acoustic emission from stresses in the member at point P.

FIG. 8 illustrates a set of signals that might be received from five of the transducers of FIG. 3 due to a noise burst from a flaw at point P in the structure 26. The noise burst is assumed to take place at time $t_0$. At time $t_1$ a signal arrives at the closest transducer T21, at time $t_2$ a signal arrives at T30, at time $t_3$ a signal arrives at T29, at $t_4$ a signal arrives at T22, and at $t_5$ a signal arrives at T21. At later times reflected signals will also arrive at these transducers. The farther away the transducer, the smaller will be the signal due to the attenuation in the wall of the vessel. If these signals are recorded in analog or digital form the location of the flaw can be calculated by knowing only time $(t_2-t_1)$ and $(t_3-t_1)$. Time $(t_1-t_0)$ is not known. Such a computation can be done with a hand calculator or with a computer that is properly programmed. If noise burst occurs at frequent intervals, then signals from adjacent pairs of transducers can be cross correlated to obtain times $(t_2-t_1)$, $(t_3-t_1)$, $(t_4-t_1)$, etc.

Figure 9:
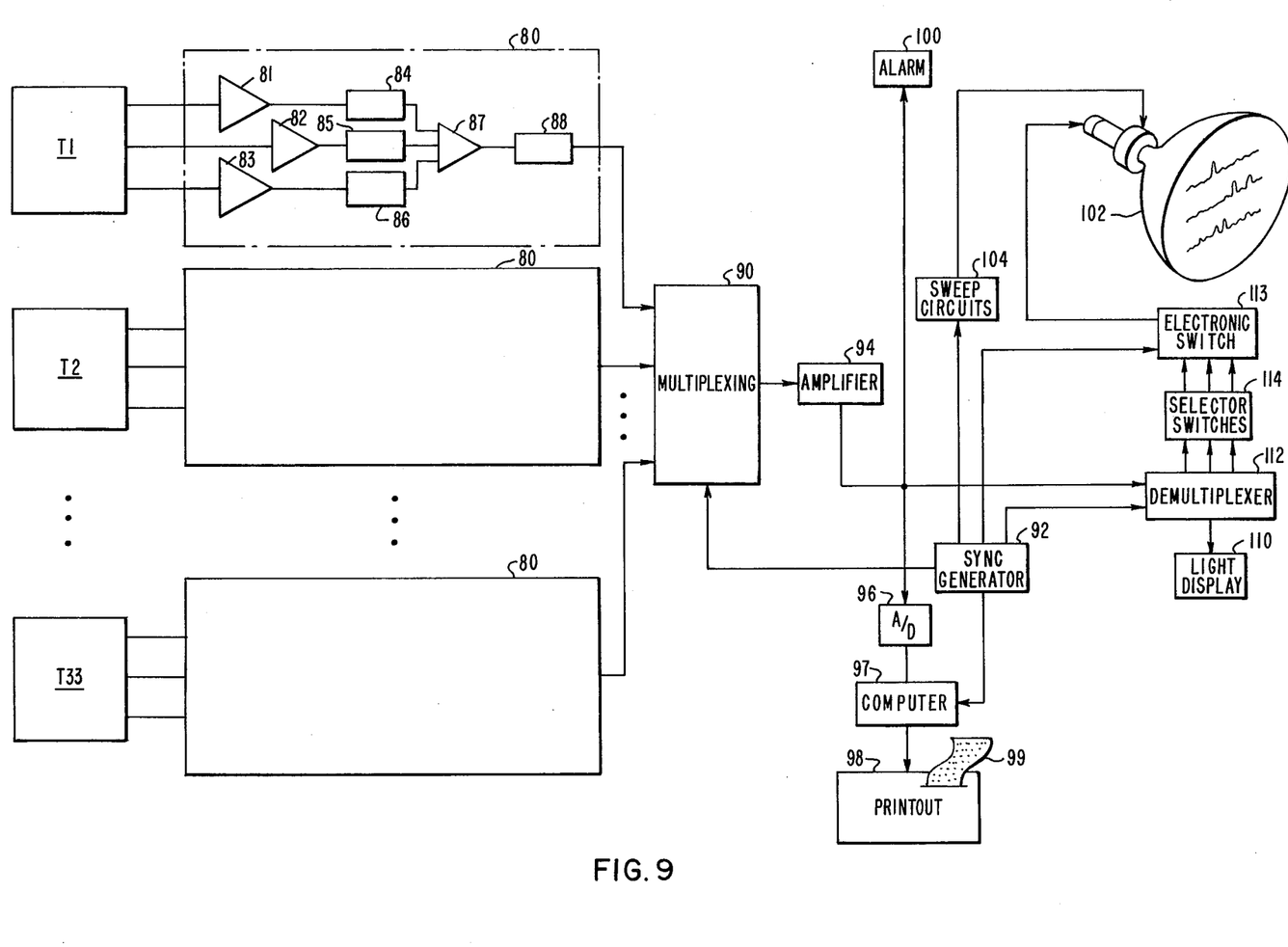
FIG. 9 is a block diagram illustrating one type of signal processing arrangement providing certain readouts of the condition of a member under test.

By way of example FIG. 9 illustrates a simple acoustic monitoring system in which the average power received by each transducer is displayed, three different types of displays being illustrated by way of example.

In the example, let it be assumed that a set of 33 transducers T1 to T33 are utilized. The three output signals from each transducer are fed to respective signal processing circuits 80 each similar in many respects to that illustrated in FIG. 7 in the inclusion of respective amplifiers 81, 82 and 83 providing their output signals to detector and squarer circuits 84, 85 and 86 the outputs of which are provided to summing circuit 87, combining the function of summers 75 and 77 of FIG. 7 to provide a combined, or output power signal. Means are provided for integrating the output from the summing circuit 87 such as by inclusion of a low pass filter 88. The resulting signal then is the integrated signal voltage associated with a particular transducer over a given time interval and is proportional to the power received at that transducer.

The processed transducer signals are all provided to a sample or multiplexing switch 90 which is under control of a sync generator 92 whereby each signal is quickly sampled and provided to an amplifier 94.

In one embodiment the signals are converted to digital form in analog to digital converter 96 and fed to a computer 97 under control of the sync generator 92. Computer 97 includes storage registers which enable it to calculate the average power received by each transducer over various periods of time such as over a period of 2.5 minutes, one hour, and one day, by way of example. The results of the calculation are provided a printout circuit 98 which may be an ordinary teletype machine providing a strip chart output 99.

Figure 10:
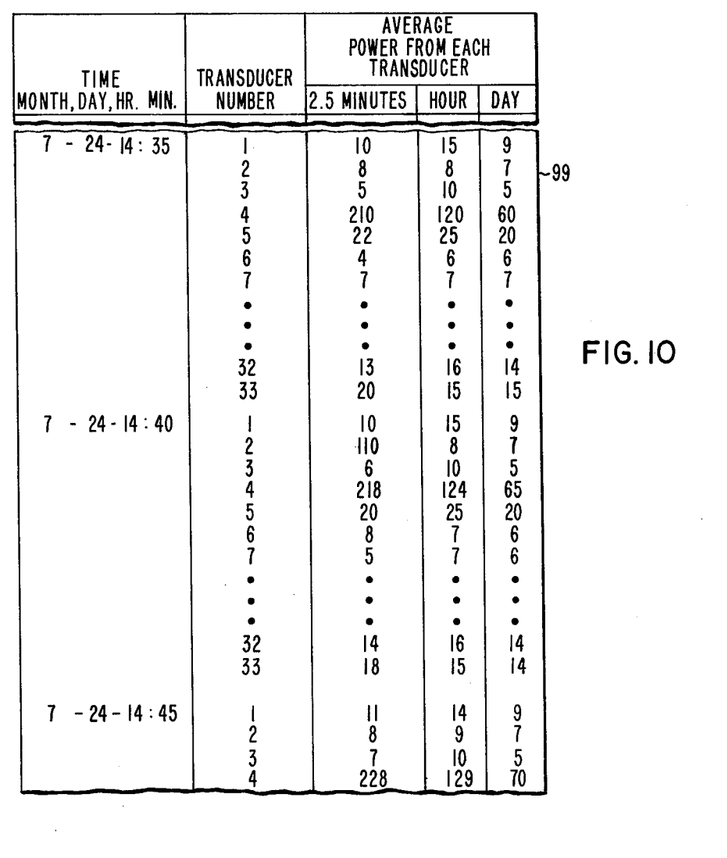
FIG. 10 is a view of a typical strip chart readout derived from the apparatus of FIG. 9.

A typical strip chart record is illustrated in FIG. 10 to which reference is now made. In the example of FIG. 10, every 2.5 minutes a new set of output levels are given for each transducer. For each transducer the average power is given over the last 2½ minutes, over the last hour, and over the last day. The power units are arbitrary and in the example, averages of 0 to 20 are considered normal, values over 100 are cause for concern and values over 500 require immediate action. In the three time intervals shown unit number 4 has indicated cause for concern because both the 2.5 minutes and one hour averages are over 100 and the daily average is increasing. Unit number 2 jumped to 110 units at 14:40 but by 14:45 was down to 8 so is not likely to be a cause for alarm. The time scales used and the alarm levels will depend upon the nature of the device under test, the danger involved due to a rupture, and experience obtained with each type of application. For example vessels to be used for nuclear reactors can be tested under pressure to determine the amplitude and duration of acoustic emission prior to structural damage.

Referring once again to FIG. 9, the alarm threshold may be provided by alarm network 100 connected to the output of amplifier 94 and being operable to provide an audible signal upon the occurrence of a signal level from amplifier 94 above a predetermined threshold.

Another type of display included in FIG. 9 is a light display panel 110 which includes a plurality of lights corresponding to the plurality of transducers utilized, with a signal derived from each of the transducers being provided to respective lights on the display 110. For example, and with reference to FIG. 11, the light display 110 illustrated in more detail is seen to include a plurality of lights designated T'1 to T'33 shown in relation to the pressure vessel of FIG. 3, which on the display, is shown to be planar. Each light is of the type which will provide a brightness which is some function the average power output of the transducer associated with that location. When the integrated output from any transducer becomes large due to a large number of moderate amplitude received pulses, or due to a few large amplitude pulses then the audio alarm will signal the operator of possible danger. He will then look at the display to determine the location and amplitude of the acoustic emission.

FIG. 9 illustrates a demultiplexer unit 112, under the control of the sync generator, as providing the outputs of the transducers to the display panel 110. Alternatively, the 33 transducer signals for display 110 can be obtained directly from the outputs of respective signal processing circuits 80 thus eliminating the need for demultiplexer 112.

Another type of readout provided in FIG. 9 is a single beam cathode ray tube (CRT) 102 with an associated electronic switch 113 that displays three acoustic signals as a function of time.

After viewing unit 110, an operator can choose any three of the 33 transducer locations of interest with three selector knobs on unit 114. A comparison of these three signals will aid the operator in pinpointing a region of high stress which is emitting acoustic signals. The horizontal sweep circuit generator 104 and the electronic switch 113 receive appropriate synchronizing signals from unit 92. The three traces on the CRT will be similar to three of the traces shown in FIG. 8.

Figure 11:
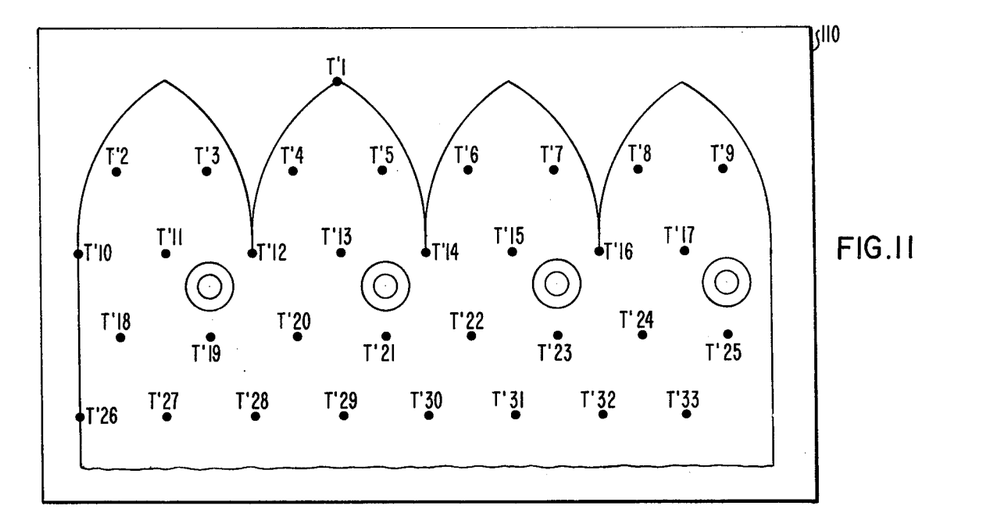
FIG. 11 is a more detailed view of the light display output of FIG. 9.

If it is desired to know both the shear wave activity and longitudinal wave activity the light display 110 may be modified to include for each transducer location a pair of light sources, for example of two different colors whereby a shear output signal from summer 77 of FIG. 7 may be provided for one light source and the compressional output signal from detector and squarer 70 of FIG. 7 may be provided to the other light source.

The monitoring system of FIG. 9 does not require the calculation of any differences in arrival times of various signals such as illustrated in FIG. 8 nor does it require any cross correlation of received signals. Once an area of high acoustic emission has been found, the precise location of the noise source can be determined by the methods previously mentioned.

Figure 12:
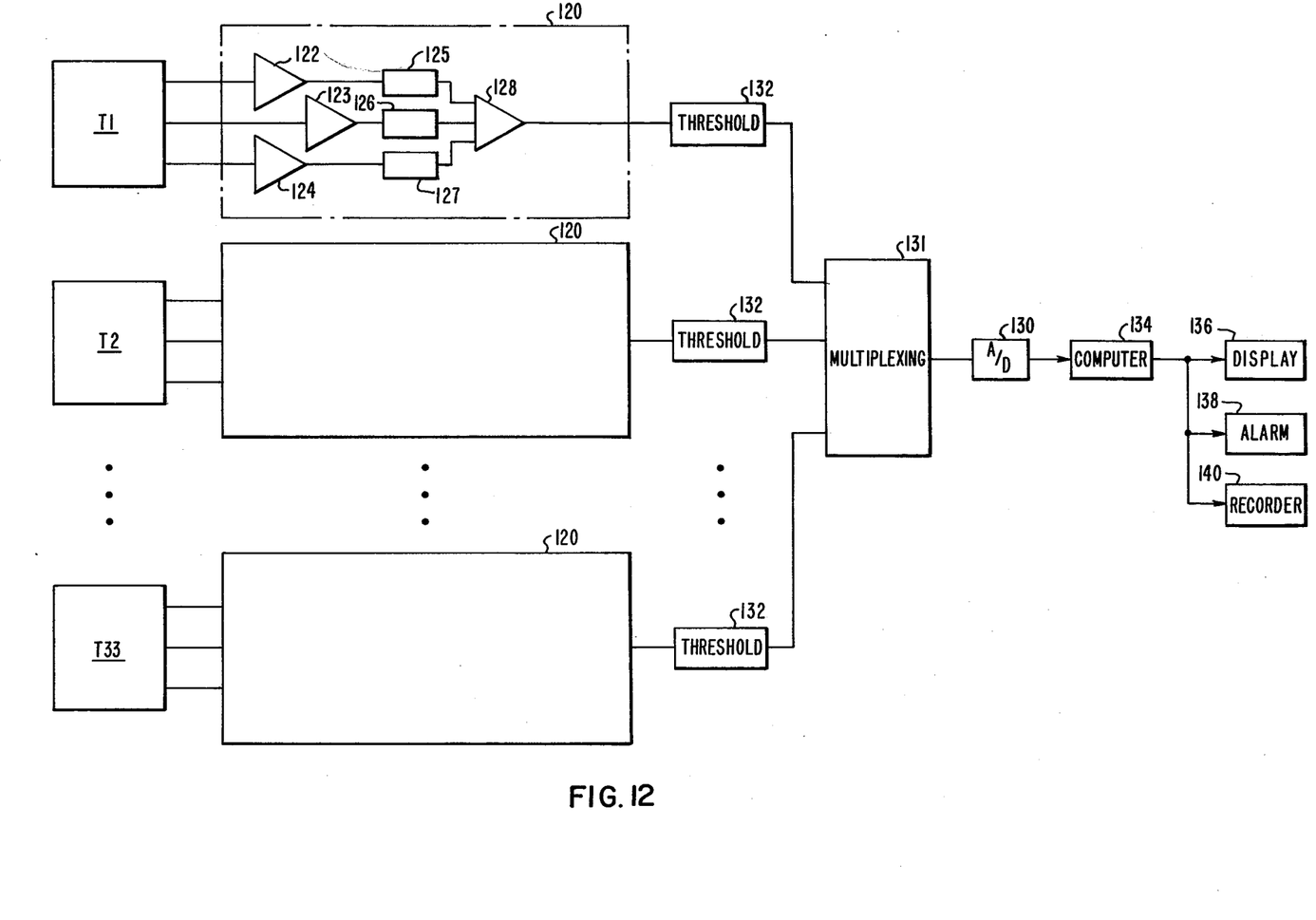
FIG. 12 is a block diagram illustrating another type of signal processing which may be performed.

FIG. 12 however illustrates a system in which the source of acoustic noise may be pinpointed with a greater accuracy than the system described in FIG. 9. Each of the transducer T1 to T33 provide their respective output signals to signal processing circuits 120 each including amplifiers 122, 123 and 124 providing respective output signals to detector and squarer circuits 125, 126 and 127 the outputs of which are summed in summing circuit 128.

In order to eliminate relatively low powered signals representing an unwanted noise factor, the output signal from each of the summers 128 will be provided to analog to digital circuit 130 only if above a predetermined threshold value as determined by threshold circuits 132. A multiplexing unit 131 samples all 33 signals in sequence to obtain a single analog signal which is converted to digital form in analog to digital circuit 130 and then provided to a computer or other signal processing network 134 for any one of a number of triangulation techniques which may be performed for determining the location of the acoustic emission. The triangulation technique may include a cross correlation of the signals, a well known technique which basically multiplies various combinations of two signals together while applying a time delay in order to obtain a maximum output signal. If two signals are the same and they are multiplied together a maximum output will be provided whereas if the signals are completely different a minimum output signal will be provided. While two signals under investigation are being multiplied together the cross correlation will delay one relative to the other until the maximum output is obtained and the particular delay which gave that maximum can be used for triangulation purposes.

If an acoustic emission above the threshold has taken place, computer 134 will provide an indication thereof on the display 136 and may provide an alarm indication thereof by means of an alarm circuit 138. A recorder 140 may also be provided to log a permanent indication of the location of the acoustic emission whereupon further diagnostic procedures may be initiated.

We claim as our invention:
1. Instrumentation for detection of acoustic emissions from a structure, comprising:
   (A) a transducer housing adapted to be placed on said structure and having an acoustic window for transmission of acoustic energy;
   (B) a piezoelectric transducer element positioned relative to said window to be responsive to acoustic energy transmitted therethrough;
   (C) said transducer element including a longitudinal axis perpendicular to said window and being poled in the same direction as said axis;
   (D) said transducer element including top, bottom, and side surfaces and having
      (i) a first pair of electrodes disposed on said top and bottom surfaces and being responsive to compressional wave energy transmitted through said window to provide a first signal,
      (ii) a second pair of electrodes disposed opposite one another on said side surface and being responsive to shear wave energy transmitted through said window to provide a second signal,
      (iii) a third pair of electrodes disposed opposite one another on said side surface and being angularly displaced relative to said second pair of electrodes and being responsive to shear wave energy transmitted through said window to provide a third signal.
2. Apparatus according to claim 1 wherein:
   (A) said third pair of electrodes are angularly displaced by 90° relative to said second pair.
3. Apparatus according to claim 1 wherein:
   (A) said transducer element is circularly cylindrical.
4. Apparatus according to claim 1 wherein:
   (A) said side surface has four faces each perpendicular to an adjacent face.
5. Apparatus according to claim 1 which includes:
   (A) a first electrically insulating disc member positioned between, and in contact with, said bottom surface of said piezoelectric transducer element and said window; and
   (B) a second electrically insulating disc member positioned on said top surface of said transducer element.
6. Apparatus according to claim 5 wherein:

(A) said first disc is bonded to said window.

7. Apparatus according to claim 5 wherein:

(A) said second disc has a plurality of apertures therein for conduction signal leads.

8. Apparatus according to claim 5 wherein:

(A) said housing is metallic; and (B) said first and second discs have equal thicknesses.

9. Apparatus according to claim 1 which includes:

(A) means for amplifying said first, second, and third signals; and (B) means for squaring and summing said amplified signals to provide a signal proportional to the total power received by said transducer element.

10. Apparatus according to claim 9 wherein:

(A) said means for amplifying includes three balanced amplifiers.

11. Apparatus according to claim 9 which includes:

(A) means for summing the squared amplified second and third signals to provide a signal proportional to the total shear wave power received by said transducer element.

12. Apparatus according to claim 9 which includes:

(A) an array of said elements;

(B) circuit means for integrating said signal proportional to total power, from each said element of said array;

(C) means for sampling each said integrated signal; and (D) means for displaying said sampled signals.

13. Apparatus according to claim 12 wherein said means for displaying includes:

(A) means for averaging the sampled signals from each said element over a number of different time intervals; and (B) means for displaying said averages.

14. Apparatus according to claim 13 wherein:

(A) said means for displaying is a chart printout.

15. Apparatus according to claim 13 which includes:

(A) an audio alarm system for providing an alarm in the event that a sampled average exceeds a predetermined threshold.

16. Apparatus according to claim 13 wherein said means for displaying includes:

(A) a display panel having a flattened view of the structure under test;

(B) said display panel including an array of light sources disposed at locations on said flattened view corresponding to transducer element locations on said structure.

* * * * *